(12) United States Patent
Gellman et al.

(10) Patent No.: US 8,915,872 B2
(45) Date of Patent: *Dec. 23, 2014

(54) MEDICAL SLINGS

(71) Applicant: Boston Scientific Scimed, Inc., Maple Grove, MN (US)

(72) Inventors: Barry N. Gellman, North Easton, MA (US); Jozef Slanda, Milford, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/665,312

(22) Filed: Oct. 31, 2012

(65) Prior Publication Data

US 2013/0303839 A1 Nov. 14, 2013

Related U.S. Application Data

(63) Continuation of application No. 13/213,774, filed on Aug. 19, 2011, now Pat. No. 8,303,526, which is a continuation of application No. 13/007,090, filed on Jan. 14, 2011, now Pat. No. 8,007,452, which is a continuation of application No. 12/843,478, filed on Jul. 26, 2010, now abandoned, which is a continuation of application No. 11/159,988, filed on Jun. 23, 2005, now Pat. No. 7,762,969, which is a continuation of application No. 10/092,872, filed on Mar. 7, 2002, now Pat. No. 6,953,428.

(60) Provisional application No. 60/274,843, filed on Mar. 9, 2001, provisional application No. 60/286,863, filed on Apr. 26, 2001.

(51) Int. Cl.
*A61F 5/00* (2006.01)

(52) U.S. Cl.
USPC .................................................. 602/4; 600/29

(58) Field of Classification Search
USPC ............. 128/885, DIG. 25; 600/29–30; 602/4
See application file for complete search history.

(56) References Cited

U.S. PATENT DOCUMENTS

| | | | |
|---|---|---|---|
| 2,973,859 A | 3/1961 | Schladermundt et al. | |
| 5,257,692 A | 11/1993 | Heacox | |
| 5,368,602 A * | 11/1994 | de la Torre | 606/151 |
| 5,899,909 A | 5/1999 | Claren et al. | |
| 6,010,447 A * | 1/2000 | Kardjian | 600/29 |
| 6,042,534 A | 3/2000 | Gellman et al. | |
| 6,306,079 B1 * | 10/2001 | Trabucco | 600/30 |
| 6,475,139 B1 | 11/2002 | Miller | |
| 6,638,210 B2 | 10/2003 | Berger | |
| 8,007,452 B2 * | 8/2011 | Gellman et al. | 602/4 |
| 2003/0179958 A1 * | 9/2003 | Chiang et al. | 383/38 |
| 2004/0015048 A1 | 1/2004 | Neisz et al. | |

\* cited by examiner

*Primary Examiner* — Michael A. Brown

(57) ABSTRACT

A medical sling made from material that is suitably shaped for use in a medical application has sides, portions of which are smoothed to prevent abrasion of surrounding tissue.

20 Claims, 2 Drawing Sheets

MEDICAL SLINGS

CROSS REFERENCE TO RELATED APPLICATIONS

This application is a continuation of U.S. application Ser. No. 13/213,774, filed on Aug. 19, 2011, now U.S. Pat. No. 8,303,526, which is a continuation of U.S. application Ser. No. 13/007,090, filed on Jan. 14, 2011, now U.S. Pat. No. 8,007,452, which is a continuation of U.S. application Ser. No. 12/843,478, filed on Jul. 26, 2010, now abandoned, which is a continuation of U.S. application Ser. No. 11/159,988, filed on Jun. 23, 2005, now U.S. Pat. No. 7,762,969, which is a continuation of U.S. application Ser. No. 10/092,872, filed on Mar. 7, 2002, now U.S. Pat. No. 6,953,428, which claims the benefit of U.S. Provisional Application No. 60/274,843, filed on Mar. 9, 2001 and U.S. Provisional Application No. 60/286,863 filed on Apr. 26, 2001, the entire contents of which are incorporated by reference herein.

TECHNICAL FIELD

This invention generally relates to surgical mesh for use as a medical sling, such as a pelvic floor repair mesh, methods of making such mesh, kits including such mesh, and methods of treating or reinforcing a damaged, prolapsed, weakened or herniated portion of a patient's body using such mesh.

BACKGROUND INFORMATION

Surgical prosthetic mesh has been used to treat or reinforce tissues or organs which have been damaged, prolapsed, weakened, or otherwise herniated, such as in the conditions rectocele, cystocele, enterocele, vaginal prolapse, and protocele, for example. A prolapse refers to the slipping down of an organ or organ part from its normal position. For example, a prolapse of the rectum refers to the protrusion of the inner surface of the rectum through the anus. Rectocele is the prolapse of the rectum into the perineum. A prolapse of the uterus refers to the falling of the uterus into the vagina due to stretching and laxity of its supporting structures. Vaginal vault prolapse refers to the prolapse of the cephalad extreme of the vaginal canal toward, through, and beyond the introitus. Cystocele (i.e., vesicocele) is a hernia formed by the downward and backward displacement of the urinary bladder toward the vaginal orifice, due most commonly to weakening of the musculature during childbirth. However, any abnormal descent of the anterior vaginal wall and bladder base at rest or with strain is considered cystocele. Enterocele is a hernia of the intestine, though the term is also used to refer specifically to herniation of the pelvic peritoneum through the rectouterine pouch (i.e., posterior vaginal, rectovaginal, cul-de-sac, or Douglas' pouch hernia).

Surgical mesh may also be used to suspend tissues or retract body organs temporarily, e.g., during surgery. For example, U.S. Pat. No. 4,973,300 describes the use of a cardiac sling for supporting the heart during surgery; and U.S. Pat. No. 5,362,294 describes the retraction of body organs such as the uterus or bowel during laparoscopic surgery; U.S. Pat. No. 6,102,921 describes the use of a medical anastomosis sling for the use in repair or regeneration of nerves.

Synthetic mesh materials utilized as slings for the treatment or reinforcement of patient tissues for these and many other conditions can cause patient complications such as erosion, due at least in part to the sharp tangs on the edges of the mesh, which are formed during the manufacturing process or afterward (for example, when a physician cuts or shears or otherwise shapes the material). These tangs can cause an irritative effect which can lead to an erosion when they contact surrounding tissue. Thus, a need exists for a sling which minimizes irritation and erosion of the tissue surrounding the tissue which it supports.

Stress urinary incontinence (SUI), which primarily affects women, is a condition which is successfully treated using surgical slings. Stress urinary incontinence is generally caused by two conditions that may occur independently or in combination, namely, intrinsic sphincter deficiency (ISD) and hypermobility. In ISD, the urinary sphincter valve, located within the urethra, fails to close properly (coapt), causing urine to leak out of the urethra during stressful actions. Hypermobility is a condition in which the pelvic floor is distended, weakened or damaged, causing the bladder neck and proximal urethra to rotate and descend in response to increases in intra-abdominal pressure (e.g., due to sneezing, coughing, straining, etc.), resulting in insufficient response time to promote urethral closure and, consequently, in urine leakage and/or flow.

Biological factors that can affect hypermobility include: poor endopelvic fascia muscle tone (from age or limited activity), endopelvic fascia muscle stretch/tear from trauma (e.g. childbirth), endopelvic fascia/arcus tendenious (muscle/ligament) separation (lateral defect), hormone deficiency (estrogen), concombinant defects (cystocele, enterocele, ureteral prolapse), and vaginal prolapse. Traditional treatment methods include bladder neck stabilization slings in which a sling is placed under the urethra or bladder neck to provide a platform preventing over distention. An emerging alternative treatment is the placement of a mid-urethral sling. Such a sling placement takes advantage of the hypermobillty condition by providing a fulcrum about which the urethra and bladder neck will rotate and provide a "urethral kink" to assist normal urethral closure.

Slings are traditionally placed under the bladder neck to provide a urethral platform limiting endopelvic fascia drop while providing compression to the urethral sphincter to improve coaptation. The mid-urethral placement location provides mechanical stability to a less moveable anatomical structure. Bladder neck slings have traditionally been affixed in the desired location using a bone anchoring method. Mid-urethral slings, being placed in a low mobility area, have demonstrated the effectiveness of an anchorless approach. Recognizing that minimal tension, if any, is necessary, a physician need only place the sling under the mid-urethra secured through the endopelvic fascia to permanently secure the sling in position. The sling permits immediate tissue security through the mesh openings and mesh tangs to initially maintain sling stabilization. As healing occurs, the endopelvic fascia and rectus fascia tissue re-establish vascularity and regrow into and around the knit pattern of the mesh. The sling in this procedure provides a fulcrum about which the pelvic floor will drop (taking advantage of the hypermobility condition of the patient) and a urethral "kink" or higher resistance to obstruct urine flow during high stress conditions.

Thus, while tangs can contribute beneficially to SUI treatment, they can also cause patient complications such as erosion of the vagina or urethra.

SUMMARY OF THE INVENTION

The present invention relates to surgical mesh or slings with a non-tanged (i.e., tangs are unformed, smoothed, rounded, or removed) section disposed on a portion of the sides of the mesh, methods of making such mesh, medical kits including such mesh, and methods of treating a damaged, weakened, sagging, herniated or prolapsed portion of a patient's body using such mesh.

The benefits of such a sling according to the invention include decreased tissue irritation from a non-tanged section when it is in contact with tissue, such as urethral and vaginal tissue, while promoting rapid scar tissue formation around the tanged portion of the sling. The formation of scar tissue generally adds bulk that compresses the tissue to which it is applied (e.g., the urethra), provides support to improve patient continence and inhibits or prevents movement of the placed sling following placement.

In one aspect, the invention involves a sling for use in a medical application. The sling is made of a mesh material that includes first and second opposed ends (i.e., disposed opposite and away from each other) along a longitudinal axis. The mesh material also includes first and second opposed sides separated by a distance along an axis perpendicular to, or substantially perpendicular to, the longitudinal axis. The perpendicular axis intersects the longitudinal axis at the midpoint, or substantially at the midpoint, of the perpendicular axis. A portion of the first and second sides and the first and second ends of the material contains tangs. A portion of the first and second sides does not contain tangs (e.g. tangs on the first and second sides are unformed, smoothed, rounded or removed), creating a non-tanged section. The first and second sides may each have, for example, a non-tanged section about 1 cm to about 5 cm in length, centered along the longitudinal axis.

The sling of the invention may have a shape suitable for a medical application; e.g., it may be rectangular or substantially rectangular. Alternatively, the sling may be octagonal, hexagonal, trapezoidal, elliptical, or some other shape that is suitable to the sling's intended placement location within the body.

In another aspect, the invention relates to a method of making a sling by direct manufacturing with a non-tanged section or by smoothing, rounding or removing the tangs on a portion of the sling to create a non-tanged section.

The sling material provided may be derived from synthetic materials or a combination of mammalian tissue(s) and synthetic material(s). The method of making the sling can further comprise sterilizing the sling material according to methods known in the art so that the sling is suitable for use in various medical applications, and may include packaging the sling in a sterile holder. The sling material may be enclosed within a sleeve to assist in handling the sling and/or to adjust the sling during surgical placement, or to prevent the sling from stretching or becoming misshapen due to handling prior to placement within the body of the patient.

In a further aspect, the invention involves a method of treating a damaged portion of a patient's body using a sling with a non-tanged section. The sling is placed inside the body of a patient such that its perpendicular axis lies substantially along a portion of the patient's body, such as the mid-urethra, bladder, rectum, vagina, blood vessel, nerve, heart, etc.; the material supports a portion of the patient's body in a manner which does not erode the surrounding tissue. The sling may be centered at the damaged portion of a patient's body using the perpendicular axis of the sling as a guide. Pressure may be distributed evenly on a portion of a patient's body with the secured sling material. A surgical fastener such as a suture, a clip, a bone anchor, a staple, or other suitable fastener, may be employed to secure the sling to anatomical structures.

The sling material may be implanted to treat female urinary incontinence according to transvaginal, transabdominal, or combined transvaginal and transabdominal procedures. For example, the method may be employed to treat a patient with SUI, the non-tanged section of the sling placed adjacent the patient's mid-urethra.

BRIEF DESCRIPTION OF THE DRAWINGS

In the drawings, like reference characters generally refer to the same parts throughout the different views. The drawings are not necessarily to scale, but rather illustrate the principles of the invention.

DESCRIPTION

Figure 1:
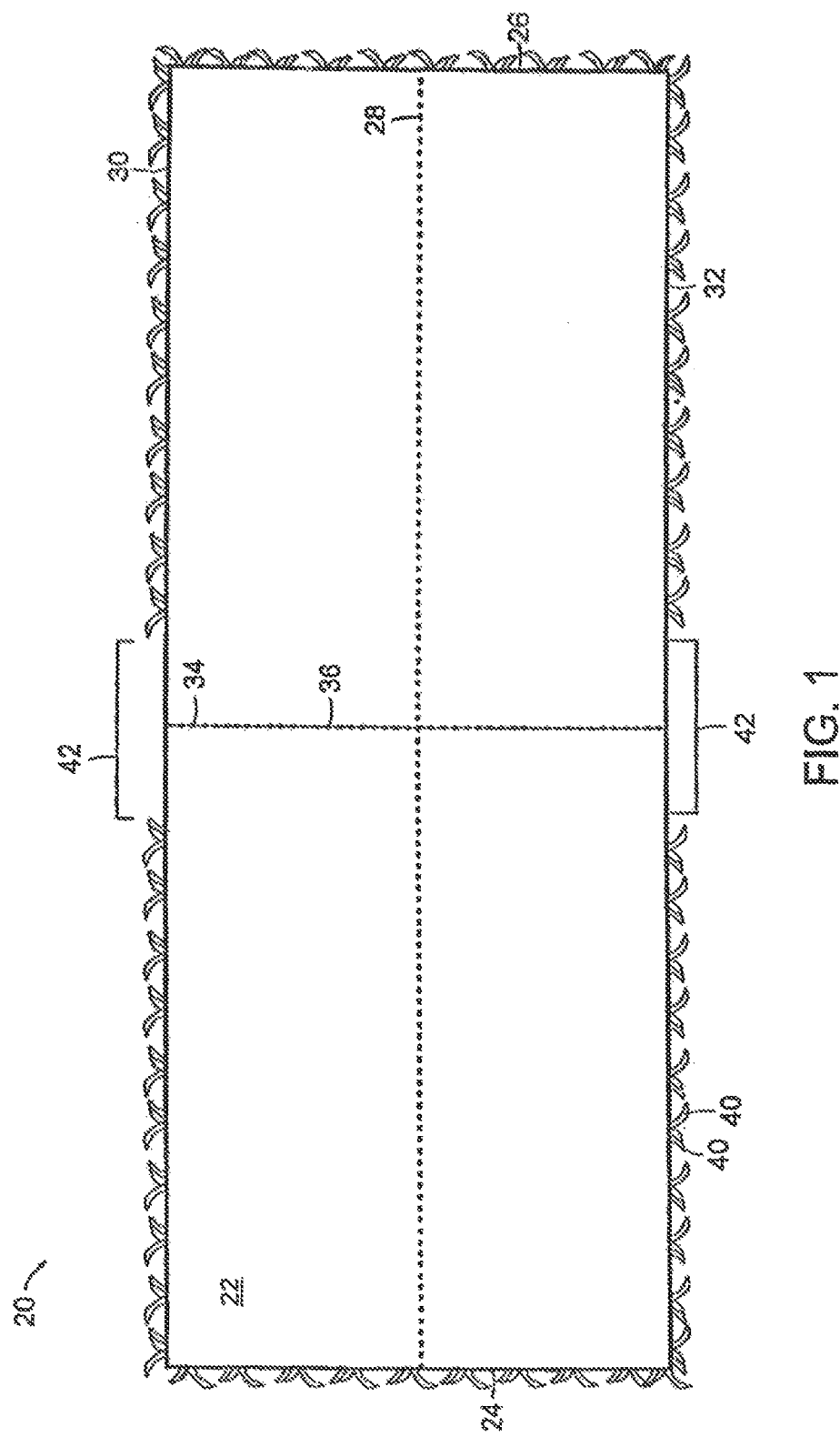
FIG. 1 is a plan view of a rectangular embodiment of a sling having a non-tanged section on either side of the perpendicular axis.

Referring to FIG. 1, a sling 20 in accordance with the present invention can be made of one or more materials 22, and includes a first end 24 and a second end 26. The second end 26 is disposed opposite and away from the first end 24 along a longitudinal axis 28. The material 22 also includes a first side 30 and a second side 32. The second side 32 is disposed opposite and away from the first side 30 along a perpendicular axis 34. The axis 34 is perpendicular to, or substantially perpendicular to, the longitudinal axis 28, and intersects the longitudinal axis 28 at the midpoint, or substantially the midpoint, of the axis 28. The longitudinal axis 28 of the sling 20 may range from about 2.5 cm to about 45 cm in length, while the perpendicular axis 34 may range from about 1.0 cm to about 3.0 cm. The sling is preferably 20 to 30 cm in length and 1 to 3 cm wide, though larger and smaller slings are contemplated depending upon the size of the patient and the surface area of the body part that requires support.

The sling 20 and 21 can be rectangular, as illustrated in FIG. 1, or substantially rectangular in shape (e.g., octagonal). Alternatively, the sling may have another shape (e.g., trapezoidal, hexagonal, or elliptical) suitable to its intended placement location within the body. Exemplary shapes are described in U.S. Pat. No. 6,042,534, the disclosure of which is incorporated herein by reference.

The thickness of the sling material 22 can be uniform over the entire piece of the material or it can vary at one or more different locations. The thickness of sling material 22 may range from about 0.02 to about 0.10 cm, but typically will be about 0.07 cm and have a uniform thickness. The material construction may impact the material thickness and uniformity; for example, a weave may have thicker regions where the fibers intersect.

The mesh may have any of a number of knits, weaves, or braids, such as those described in U.S. Pat. Nos. 5,569,273; 5,292,328; 5,002,551; 4,838,884; 4,655,221; 4,652,264; 4,633,873; 4,520,821; 4,452,245; 4,347,847; 4,193,137; 5,124,136; 3,054,406; and 2,671,444 the disclosures of which are hereby incorporated by reference.

Figure 2:
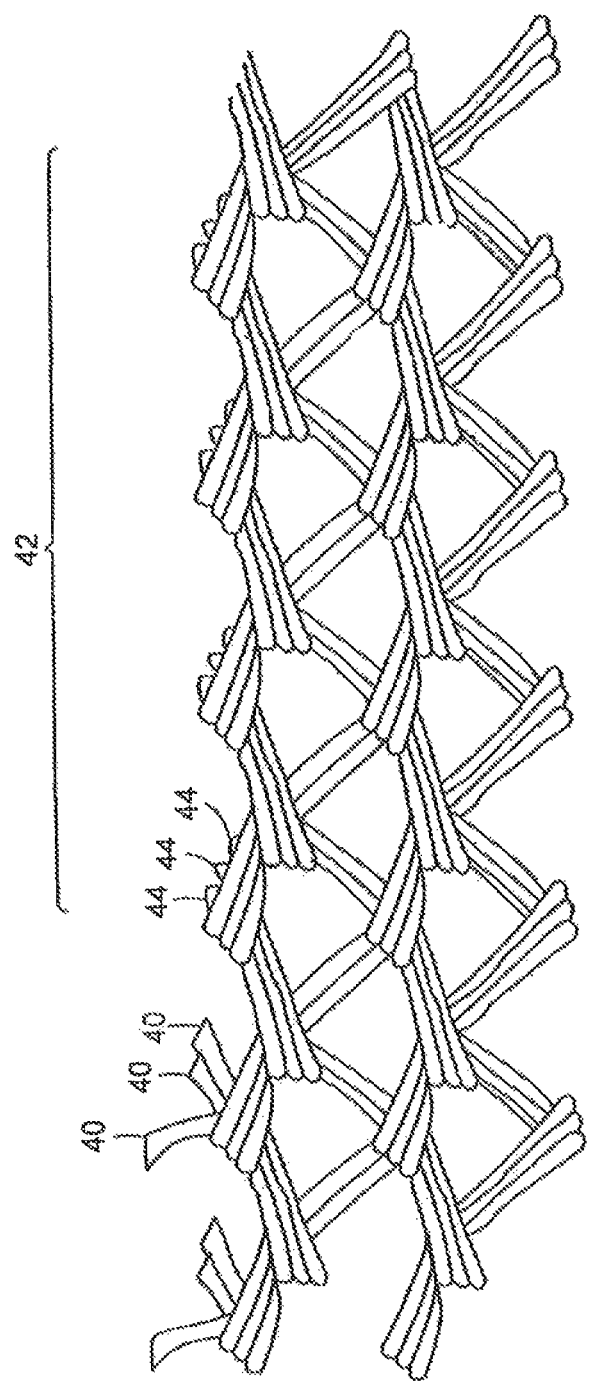
FIG. 2 is a close-up diagram of sling material with a non-tanged section.

The mesh material may be fabricated from any of a number of biocompatible materials such as nylon, polyethylene, polyester, polypropylene, fluoropolymers, copolymers thereof, combinations thereof, or other suitable synthetic material(s). The material may be, for example, a synthetic material that is absorbable by the patient's body. Suitable absorbable synthetic materials include polyglycolic acid, polylactic acid, and other suitable absorbable synthetic materials. The mesh material may be fabricated from one or more yarns, which yarns may be made from one or more materials. The mesh may be produced according to numerous fabrication processes, and may be designed to permit rapid tissue revascularization and tissue in-growth by having large interstitial spaces. For example, each yarn of the mesh may have void areas between yarn filaments and the fabrication process may create crevices. An exemplary weave is a tricot knit with two yarns per needle, as illustrated in FIG. 2. In a preferred embodiment, the mesh is composed of polypropylene monofilament yarns.

Absorbable synthetic materials may also be suitable for use in accordance with the invention. Such absorbable synthetic materials include, for example, polyglycolic acid (PGA), polylactic acid (PLA), and other available absorbable synthetic materials. A suitable PGA material is available under the trade designation DEXON, from TYCO. Other suitable polymeric and non-polymeric synthetic materials may be employed in accordance with the invention. Exemplary materials as set forth above are found in U.S. Pat. Nos. 6,090,116; 5,569,273; 5,292,328; 4,633,873; 4,452,245; 4,347,847; 3,124,136; 3,054,406; and 2,671,444, and Inglesia, C. B. et al. (1997) Int. Urogynecol. J. 8:105-115, the entire disclosures of which are incorporated by reference.

Alternatively, the sling material 22 may be derived from a combination of mammalian tissue(s) and synthetic material (s). The mammalian tissue source may be, for example, human, human cadaveric, or tissue-engineered human tissue. The mammalian tissue may alternatively be from an animal source such as porcine, ovine, bovine, and equine tissue sources. Such combinations may also include materials that include both synthetic polymers and animal cells that are treated so as to cross-link the collagen or other commonly antigenic fibers of the animal cells. In one embodiment, at least a portion of the mesh portion of the sling which contacts the patient's tissue comprises a synthetic material requiring smoothness of the tangs.

The tangs (i.e., sharp projections or frayed edges) 40 that form when the material 22 is cut, chopped, torn, frayed or otherwise manufactured may be located along any edge of the material 22. The tangs 40 are generally useful for encouraging tissue growth into the material 22. However, it is found that some tangs 40 may erode the adjacent tissue when the sling 20 is inserted into a patient's body. Accordingly, a portion of the tangs 40 located on sides 30 and 32 (e.g., in some embodiments to within about 1 cm to about 5 cm of either side of the perpendicular axis 34) are therefore unformed, smoothed, rounded or removed to form a non-tanged section 42. By removing these irritative projections, which will be in close proximity to the urethra and anterior vaginal wall, the erosion effects are reduced.

With continued reference to FIG. 1, in one version of the sling, a line 36 is disposed along the perpendicular axis 34 of a rectangular sling 20. The line 36 may be formed by, for example, applying surgical ink along the perpendicular axis 34 of the material 22. Preferably, the approximate midpoint of the non-tanged sections 42 of sides 30 and 32 intersects with line 36. Thus, line 36 may be employed as a visual guide to evenly align the non-tanged sections 42 with the portion of the patient's body that the sling 20 is employed to support.

Any process which will smooth, round or remove the tangs 40 to remove their sharp edges is suitable. For example, the tangs 40 may be heat smoothed by burning or melting. Such a heat process causes melting of the sharp tangs 40 back to the woven knot 44 forming a non-tanged section 42, as shown best in FIG. 2. The non-tanged section 42 may be located on both sides 30 and 32, occupying, for example, about 1 to 4 cm on either side of the perpendicular axis 34. The tangs may be removed, for example, along a 5, 6, 7, 8, 9 or 10 cm portion of the side of the mesh material.

An exemplary method of making a sling 20 of the invention from a material 22, for example, includes manufacturing a sling material 22 and forming a non-tanged section 42 on a portion of a material 22 at sides 30 and 32 adjacent the perpendicular axis 34. The sling 20 may be formed from the cutting to size of a larger piece of sling material 22. The tangs 40 on a portion of each side 30 and 32 are unformed, smoothed, rounded or removed (e.g., to the woven knots) to form a non-tanged section 42. The non-tanged section 42 may span a segment of sides 30 and 32 having a length up to about 4 cm, but usually at least about 1 cm, and the segment is preferably centered on the perpendicular axis 34. In alternative embodiments, the non-tanged section 42 may span a segment of sides 30 and 32 having a length of 5, 6, 7, 8, 9 or 10 cm. In one version of the method, the tangs 40 are smoothed, rounded or removed by exposing the tangs to a source of heat (i.e., by contact or by bringing the heat source into close proximity to the tangs). In an alternative method, a straight blade edge that is heated to a sufficient temperature to simultaneously cut and smooth the tangs 40 may be employed.

The sling 20 may be surrounded by or enclosed within a sleeve or envelope as described in the U.S. patent application entitled "System for Implanting an Implant" co-filed with the instant application, which is hereby incorporated by reference in its entirety. The co-filed application also contains methods for installing slings enclosed within an envelope.

Referring to FIG. 1, the sling 20 may be pre-soaked in a prescribed drug prior to implantation in a patient's body. Exemplary drugs include neomycin, sulfa drugs, antimicrobials, and antibiotics, generally. In some embodiments, the hydrophilic material, the drug, or both when used in combination, release the drug to patient tissues upon contact. Thus, the drugs that are delivered to the patient tissue surfaces when accessing and inserting the sling 20 are active upon contact with the patient's tissue during implantation of the surgical device.

Alternatively, the sling 20 is made of a non-wettable material such as a polypropylene, polyethylene, polyester, polytetrafluoroethylene, TYVEK®, MYLAR®, or co-polymers thereof. Polytetrafluoroethylene, which is suitable for use in accordance with the present invention, is available from DuPont (Wilmington, Del., under the trade designation TEFLON®). Such non-wettable materials do not take up any liquids, for example, drugs in solution. In order to permit drugs to bond or absorb to these non-wettable material surfaces, the sling 20 can be treated with a substance that is wettable such as, for example, a wettable coating composition. The wettable coating composition maybe a synthetic coating (e.g., polyvinylperilidone or PVP), a natural coating (e.g., collagen) or a physically absorbent material (e.g., sponge comprising cellulose or open celled polyurethane). The wettable coating composition may be hydrophilic, so as to pick up or absorb hydrophilic drugs. Suitable hydrophilic coatings may be water soluble and include, for example, Hydroplus (Boston Scientific Corp., Natick, Mass.), Hydropass (Boston Scientific Corp., Natick, Mass.), hyoscymine sulfate, which is available under the trade designation CYTOSPAZ from Polymedica (Woburn, Mass.), and ketrodac frometharnine, which is available under the trade designation Toradol from Roche Pharmaceuticals (Nutley, N.J.). Hydrophilic drugs that may be employed in accordance with the invention include oxybutynin chloride, lidocaine, ketorolac, and hyoscymine sulfate, for example.

Similarly, a hydrophobic coating may be employed on one or more surfaces of the sling 20. Suitable hydrophobic coatings include but are not limited to hydrophobic coatings that may be employed in accordance with the invention include polytetrafluoroethylene, silicon, and Pyrelene. Such hydrophobic coatings may be used in conjunction with and absorb hydrophobic drugs. Suitable hydrophobic drugs include but are not limited to suitable hydrophobic drugs include ibuprofen, ketoprofen, diclofenac, and lidocaine in hydrophilic form. Where the bonding between these coatings and drugs is weak, the drug that is absorbed will readily release to be delivered to the surfaces it contacts. Alternatively, a stronger bonding affinity may provide a slower timed release of the drug.

Where the coating applied to the surface of the sling 20 has an ionic charge, drugs comprising a complementary charge will bond to the coating when the coating and the drug are exposed to one another. The strength of any bonding will impact how readily the drug is released from the surface of the sling 20. Where the ionic bonding between the coating and the drug is weak, the drug will release more readily. In embodiments where rapid drug release is desirable, covalent bonding between the surface coating and the drug should be avoided.

Alternatively, the sling 20 may be coated with hydrophilic coating 75. The sling 20, coated with hydrophilic coating 75, may be dipped into a solution containing a hydrophilic drug just prior to surgery. In another embodiment, the hydrophilic coating and the hydrophilic drug are mixed to form a single coating. This coating may be disposed on the surface of the sling 20.

Methods of sling delivery and installation, e.g., to treat female stress incontinence include but are not limited to transvaginal, transabdominal (percutaneous), and combined transvaginal and transabdominal procedures.

Variations, modifications, and other implementations of what is described herein will occur to those of ordinary skill in the art without departing from the spirit and the scope of the invention. Accordingly, the invention is not to be limited by the preceding illustrative description.

What is claimed is:

1. A method of treating a patient, the method comprising:
    positioning a mesh sling having a tanged section and an untanged section within the patient so that the untanged section is adjacent to a urethra of the patient.

2. The method of claim 1, wherein (a) the mesh sling includes a line comprising a surgical ink, the line disposed at a midpoint of the untanged section, and (b) the method includes aligning the line with a mid-urethra of the patient.

3. The method of claim 1, wherein the mesh sling includes a drug.

4. The method of claim 3, wherein the drug is an antimicrobial or an antibiotic.

5. The method of claim 1, wherein the mesh sling includes a first end and a second end opposite and away from the first end, and first and second sides extending between the first and second ends, and wherein each of the first and second sides includes a tanged section and an untanged section.

6. The method of claim 1, wherein the mesh sling comprises an absorbable material.

7. The method of claim 1, wherein the mesh sling comprises a nonabsorbable material.

8. The method of claim 1, wherein the mesh sling is secured through the endopelvic fascia.

9. A mesh sling for use as a surgical implant, the mesh sling comprising:
    a plurality of sides, wherein at least one side of the plurality of sides includes a first tanged portion, a second tanged portion and an untanged portion disposed between the first tanged portion and the second tanged portion.

10. The mesh sling of claim 9, further comprising a drug.

11. The mesh sling of claim 10, wherein the drug is an antimicrobial or an antibiotic.

12. The mesh sling of claim 9, wherein the mesh sling comprises an absorbable material.

13. The mesh sling of claim 9, wherein the mesh sling comprises a nonabsorbable material.

14. The mesh sling of claim 9, wherein at least two sides of the mesh sling include both tanged and untanged sections.

15. A mesh sling for use in a medical application, the mesh sling comprising:
    an untanged section; and
    a visible line comprising a surgical ink disposed within the untanged section, the visible line permitting alignment of the untanged section with a urethra of a patient.

16. The mesh sling of claim 15, wherein the mesh sling includes a drug.

17. The mesh sling of claim 16, wherein the drug is an antimicrobial or an antibiotic.

18. The mesh sling of claim 15, wherein the mesh sling includes a first end and a second end opposite and away from the first end, and first and second sides extending between the first and second ends, and wherein each of the first and second sides includes a tanged section and an untanged section.

19. The mesh sling of claim 15, wherein the mesh sling comprises an absorbable material.

20. The mesh sling of claim 15, wherein the mesh sling comprises a nonabsorbable material.

* * * * *